(12) United States Patent
Bustos De Abajo et al.

(10) Patent No.: US 7,732,397 B2
(45) Date of Patent: Jun. 8, 2010

(54) USE OF CARDIOTROPHIN IN LIVER DISEASES

(75) Inventors: Matilde Bustos De Abajo, Pamplona (ES); Jesús Prieto Valtueña, Pamplona (ES); Juan José Lasarte Sagastibelza, Pamplona (ES); Elena Baixeras Llano, Pamplona (ES)

(73) Assignee: Proyecto de Biomedicina Cima, S.L., Pamplona (ES)

( * ) Notice: Subject to any disclaimer, the term of this patent is extended or adjusted under 35 U.S.C. 154(b) by 560 days.

(21) Appl. No.: 10/798,219

(22) Filed: Mar. 11, 2004

(65) Prior Publication Data

US 2004/0224888 A1 Nov. 11, 2004

Related U.S. Application Data

(63) Continuation of application No. PCT/ES02/00445, filed on Sep. 20, 2002.

(51) Int. Cl.
*A61K 38/18* (2006.01)
*C12N 5/071* (2010.01)

(52) U.S. Cl. .......................................... 514/2; 424/93.1
(58) Field of Classification Search .................... 514/2; 424/93.1
See application file for complete search history.

(56) References Cited

U.S. PATENT DOCUMENTS 6,719,969 B1 * 4/2004 Hogaboam et al. ......... 424/85.2
2002/0187936 A1 * 12/2002 Costa et al. .................... 514/12

FOREIGN PATENT DOCUMENTS

WO  WO 95/29237      11/1995
WO  WO 00/43790  *   7/2000

OTHER PUBLICATIONS

Jin et al. (1996) Cytokine, vol. 8 (12), 920-926.*
Narayanan Menon et al. (2001) Mayo Clinic Proceedings, vol. 76 (10), 1021-1029.*
Nagy et al. (2001) Hepatology, vol. 33(2), 339-345.*
Reto A. Gadient, et al, "Leukemia Inhibitory Factor, Interleukin 6, and other Cytokines Using the GP130 Transducing Receptor: Roles in Inflammation and Injury", *Stem Cells*. (1999) vol. 17; p. 127-137.
Michihisa Jougasaka, et al, "Augmented Cardiac Cardiotrophin-1 in Experimental Congestive Heart Failure", *Circulation 2000* vol. 101; p. 14-17 (1999).
Shigemichi Hishinuma, et al, "Hypoxic Stress Induces Cardiotrophin-1 Expression in Cardiac Myocytes", *Biochemical and Biophysical Research Communications* vol. 264, (1999) p. 436-440.
A. Stephanou, et al, "Cardiotrophin-1 Induces Heat Shock Protein Accumulation in Cultured Cardiac Cells and Protects them from Stressful Stimuli", *J Mol Cell Cardiol* vol. 30, (1998) p. 849-855.
D. Pennica, et al, "Cardiotrophin-1, a Cytokine Present in Emboyronic Muscle, Supports Long-Term Survival of Spinal Motoneurons", *Neuron* vol. 17 (1996) p. 63-74.
T. Border, et al, "Adenoviral cardiotrophin-1 gene transfer protects pmn mice from progressive motor neuronopathy", *The Journal of clinical Investigation* vol. 104, (1999) p. 1077-1085.
M. Bustos, et al, "Liver Damage using Suicide Genes", *American Journal of Pathology*, vol. 157, (2000) p. 549-559.
T. Kishimoto, et al, "Cytokine Signal Transduction", *Cell* vol. 76 (1994) p. 253-262.
M. Murakami, et al, "IL-6-Induced Homodimerization of gp 130 and Associated Activation of a Tyrosine Kinase", *Science*, New Series vol. 260, (1993) p. 1808-1810.
S. Davis, et al, "LIFR# and gp130 as Heterodimerizing Signal Transducers of the Tripartite CNTF Receptor", *Science*, New Series vol. 260 (1993) p. 1805-1808.
D. Pennica, et al, "Expression cloning of cardiotrophin 1, a cytokine that induces cardiac myocyte hypertrophy", *Proc. Natl,. Acad Sci. USA* vol. 92 (1995) p. 1142-1146.
O. Robledo, et al, "Signaling of the Cardiotrophin-1 Receptor", *The Journal of Biological Chemical*, (1997 vol. 272 p. 4855-4863.
Z. Sheng, et al, "Cardiotrophin-1 displays early expression in the murine heart tube and promotes cardiac myocyte survival", *Development* vol. 122 (1996) p. 419-428.
H. Jin, et al, "Effects of Cardiotrophin-1 on Haemodynamics and Cardiac Function in Conscious Rats", *Cytokine* vol. 10 (1998) p. 19-25.
D. Latchman, "Cardiophin-1 (CT-1): a novel hypertropic and cardioprotective agent", *International Journal of Experimental Pathology*, (1999) vol. 80 p. 189-196.

(Continued)

*Primary Examiner*—Anne Marie S Wehbe
(74) *Attorney, Agent, or Firm*—Ladas and Parry LLP

(57) ABSTRACT

Use of cardiotrophin in liver diseases. The invention describes the increased expression of cardiotrophin (CT-1) during the process of hepatic regeneration coinciding with maximum proliferation of hepatocytes and the role of CT-1 as a stimulator of hepatic regeneration. Furthermore, it describes the hepatoprotective role of CT-1 in various models of acute liver damage.

The importance of using CT-1 in the manufacture of compositions for use in the treatment of hepatopathies is demonstrated. The invention describes such use in various forms and methods, including the recombinant protein and the use of the gene sequences that code for CT-1.

16 Claims, 13 Drawing Sheets

OTHER PUBLICATIONS

S. Haga, et al, Stat3 protects against Fas-induced liver injury by redox-dependent and—independent mechanisms, *The Journal of Clinical Investigation* (2003) vol. 112 p. 989-998.

M.J. Hussain, et al, "Cellular expression of tumour necrosis factor-α and interferon-γ in the liver biopsies of children with chronic liver disease", *Journal of Hepatology* (1994) vol. 21 p. 816-821.

N. Kobayashi, et al, "Prevention of Acute Liver failure in Rats with Reversibly Immortalized Human Hepatocytes", *Science* (2000) vol. 287 p. 1258-1262.

T. Kondo, et al, "Essential roles of the Fas ligand in the development of hepatitis", *Nature Medicine* (1997) vol. 3 p. 409-413.

J.J. Lasarte, et al, "A Recombinant Adenovirus Encoding Hepatitis C Virus Core and E1 Proteins Protects Mice Against Cytokine-Induced Liver Damage", *Hepatology* (2003) p. 461-470.

Y. Panis, et al, "Progressive necrosis after hepatectomy and the pathophysiology of liver failure after massive resection", *Surgery* vol. 121 (1997) p. 142-149.

N. Sheron, et al, "Increased production of tumour necrosis factor alpha in chronic hepatitis B virus infection", *Journal of Hepatology*, vol. 12 (1991) p. 241-245.

U. Spengler, et al, "Serum Levels and in Situ Expression of TNF-α and TNF-α Binding Proteins in inflammatory liver diseases", *Cytokine* vol. 8 (1996) p. 864-872.

G. Tergs et al, "A T Cell- dependent Experimental Liver Injury in Mice Inducible by Concanavalin A", *The American Society for Clinical Investigation, Inc.* (1992) vol. 90, p. 196-203.

JH Hwan, et al, "Death receptor-mediated apoptosis and the liver", *Journal of Hepatology* (2002) p. 400-410.

Peters, M. et al "A new hepatocyte stimulating factor: Cardiotrophin-1 (cT-1)" FEBS Letters, vol. 372, n°. 2-3, 1995 pp. 177-180.

Richard, C.D. et al "Mruine Cardiotrophin-1 stimulates the acute-phase response in rat hepatocytes and H35 hepatoma cells". Journal of Interferon and Cytokine Research, vol. 16. n° 1, 1996 pp. 69-75.

Robledo O. et al "Hepatocyte-derived cell ilines express a functional receptor for cardiotrophin-1". European Cytokine Network, vol. 8 n°. 3, 1997, pp. 45-252.

Hongkui, J. et al "In vivo effects of cardiotrophin-1". Cytokine, vol. 8 n°. 12, 1996, pp. 920-926.

Webber et al., In Vivo Response of Hepatopcytes to Growth Factor Requires an Initial Priming Stimulus; Feb. 1994; pp. 489-497.

Bockhorn et al.; Vascular Endothelial Growth Factor Does Not Improve Liver Regeneration and Survival After 90% Subtotal Liver Resection; Hepatology Research 2007; 37: 353-359.

Journal of Hepatology 2000; Liver Regeneration; pp. 19-31, Fausto, N.

Ghezzi et al.; Erythropoietin as an Antiapoptotic, Tissue-Protective Cytokine; Cell Death and Differentiation (2004) 11, S37-S44.

* cited by examiner

USE OF CARDIOTROPHIN IN LIVER DISEASES

This application is a continuation of copending International Application PCT/ES02/00445 filed on Sep. 20, 2002, which designated the U.S., claims the benefit thereof and incorporates the same by reference.

The invention relates to the use of cardiotrophin (CT-1) for stimulating hepatic regeneration and protecting hepatocytes from processes of apoptosis and necrosis. Accordingly this invention refers to the use of cardiotrophin for the treatment of acute, subacute, fulminant and chronic hepatitis and for the treatment of hepatic cirrhoses, as well as for promoting hepatic regeneration after hepatectomies, after liver transplantation and for stimulating the proliferation and trophism of hepatocytes or hepatocyte precursors in culture.

BACKGROUND OF THE INVENTION

The liver, both in humans and in animals, has the unique capacity of regulating its growth and its weight. If a harmful agent destroys part of the hepatic parenchyma, the surviving hepatocytes are able to replicate and thus replace the damaged parenchyma. If hepatic resection or hepatocellular lesion of viral, toxic, immunologic or metabolic origin affects a very high proportion of the parenchyma so that the regenerative capacity of the hepatic tissue that remains is exceeded, a hepatic insufficiency develops which can prove fatal. At present, no drug exists with liver-protecting and regeneration-stimulating effect that can be used in acute or chronic hepatic insufficiency. It is therefore urgent and important that the array of drugs used in hepatology should include therapeutic products for these indications. An hepatoprotective agent is a product or active principle able to protect hepatic cells against a variety of stimuli causing toxicity and/or damage in hepatocytes and ultimately necrosis or apoptosis. Thus, whenever liver damage is induced, the administration of hepatoprotective agents at the right doses will improve the survival of hepatic cells facilitating hepatic regeneration, contributing to liver function normalization and in extreme cases, to the survival of the individual. Liver damage can be induced by toxic agents (including alcohol), viruses, autoimmune disorders, ischemia, ischemia/reperfusion (as in the case of the damage induced in the liver implanted during liver transplantation) and in general by any inflammatory processes. A good hepatoprotective agent will preclude or decrease the development of liver damage and hepatic cell death in those situations.

By liver regeneration we understand the reaction of the liver to compensate a decrease in its functional mass (either decrease in tissue or cells loss) by the proliferation of normal hepatocytes until the liver mass is restored. There are several clinical settings in which liver regeneration plays an important role, including hepatic resection during surgery (partial hepatectomy or liver transplantation by live donors) or situations of liver damage as described above (toxic agents, viruses, ischemia, ischemia/reperfusion, etc). A stimulating agent of liver regeneration is an agent able to induce such hepatocellular proliferation, helping to reduce mortality related with functional mass decrease.

The present invention proposes the use of cardiotrophin in liver diseases.

Cardiotrophin (also called CHF or cardiac hypertrophy factor) has been employed previously in the treatment of cardiac disorders and neurodegenerative and neurologic diseases (WO 95/29237), as a modulator of local inflammatory processes linked to the LIFRβ receptor (WO 97/30146), in the diagnosis and treatment of tumors (WO 00/43790), and in the treatment of amyotrophic lateral sclerosis and Parkinson's disease (WO 97/39629).

The invention does not relate to any of these applications, but focuses on the uses of CT-1 in therapeutic compositions that can be used in the treatment of hepatocytes, and especially as an agent for protecting the latter against processes of apoptosis and necrosis and as an agent for stimulating hepatic regeneration in general.

CT-1 is one of the so-called neuropoietic cytokines belonging to the IL-6 family (1). The receptors of the cytokines of this family are made up of distinct subunits, but they all share the gp130 subunit (2). Some members of the family (IL-6 and IL-11) induce homodimerization of gp130 (3), whereas others such as leukemia inhibitory factor (LIF), oncostatin and ciliary neurotrophic factor (CNTF) induce heterodimerization of the gp130 subunit with the 190 kDa LIF receptor (4). The CT-1 receptor contains the gp130 chain, the β subunit of the LIF receptor (LIFRβ) and a third component known as the α subunit of the CT-1 receptor (5, 6). The latter participates in the formation of a three-part complex that confers high sensitivity and specificity to CT-1. Activation of the CT-1 receptor induces a series of intracellular signals that include the early activation of tyrosine kinases of the JAK family (JAK-1, JAK-2 and Tyk2). The main effectors of the JAKs are the group of cytosolic transcription factors STATs (STAT-1 and STAT 3; signal-transducing activators of transcription). Activation of the JAKs also signals via the Ras-MAP kinase pathway and is involved in activation of the PI3-K (phosphatidyl inositol 3-kinase) pathway (2).

CT-1 was originally identified as a hypertrophic factor in cardiomyocytes (7, 8) as it had been shown to have a role in stimulating the embryonic development of cardiomyocytes and a protective action on cardiomyocytes against apoptosis induced by hypoxia, ischemia, and damage by ischemia-reperfusion and (8, 9, 10, 11, 12). A protective effect on the myocardium has also been described in cases of heart failure (10). Other effects of CT-1 include promotion of the survival of motoneurons and dopaminergic neurons (13, 14).

BIBLIOGRAPHY

1.—Gadient R A, Patterson P H. Leukemia inhibitory factor, interleukin 6 and other cytokines using the GP-130 transducing receptor: Roles in inflammation and injury. Stem Cells 1999; 17:127-137.

2.—Kishimoto T, Taga T, Akira S. Cytokine signal transduction. Cell. 1994 Jan. 28;76(2):253-262.

3.—Murakami M, Hibi M, Nakagawa N, Nakagawa T, Yasukawa K, Yamanishi K, Taga T, Kishimoto T. IL-6-induced homodimerization of gp130 and associated activation of a tyrosine kinase. Science. 1993 Jun. 18;260 (5115):1808-1810.

4.—Davis S, Aldrich TH, Stahl N, Pan L, Taga T, Kishimoto T, Yancopoulos GD. LIFR beta and gp130 as heterodimerizing signal transducers of the tripartite CNTF receptor. Science. 1993 Jun. 18;260(5115): 1805-1808.

5.—Pennica D, King K L, Shaw K J, Luis E, Rullamas J, Luoh S M, Darbonne W C, Knutzon DS, Yen R, Chien K R, Baker J B. Expression cloning of cardiotrophin 1, a cytokine that induces cardiac myocyte hypertrophy. Proc Natl Acad Sci USA. 1995 Feb. 14;92(4):1142-1146.

6.—Robledo O, Fourcin M, Chevalier S, Guillet C, Auguste P, Pouplard-Barthelaix A, Pennica D, Gascan H. Signaling of the cardiotrophin-1 receptor. Evidence for a third component. J. Biol. Chem. 1997, 272(8): 4855-4863.

7.—Sheng Z, Pennica D, Wood W I, Chien K R. Cardiotrophin-1 displays early expression in the murine heart tube and promotes cardiac myocyte survival. Development 1996; 122: 419-426.

8.—Jin H, Yang R, Ko A, Pennica D, Wood WI, Paoni NF. Effects of cardiomiotrophin-1 on haemodynamics and cardic function in conscious rats. Cytokine 1998; 10: 19-25.

9.—Latchman D S. Cardiotrophin-1 (CT-1): a novel hypertrophic and cardioprotective agent, Int. J. Exp. Pathol. 1999; 80: 189-196.

10.—Jougsaki M, Tachibana I, Luchner A, leskinen H, Redfield M M, Burnett J C. Augmented cardiac cardiotrophin-1 in experimental congestive heart failure. Circulation 2000; 101: 14-17.

11.—Hishinuma S, Funamoto M, fujio Y, Kunisada K, Yamauchi-Takihara K. Hypoxic stress induces cardiotrophin-1 expression in cardiac myocytes. Biochem. Biophysic. Res. Commun 1999; 264: 436-440.

12.—Stephanou A, Brar B, Heads R, Knight R D, Marber M S, Pennica D, Latchman D S. Cardiotrophin-1 induces heat shock protein accumulation in cultured cardiac cells and protects them from stressful stimuli. J. Mol. Cell Cardiol. 1998; 30: 849-855.

13.—Pennica D. Cardiotrophin-1, a cytokine present in embryonic muscle, supports long-term survival of spinal motoneurons. Neuron 1996; 17: 63-74.

14.—Bordet T, Schmalbruch H, Pettmann B, Hagege A, Castelanu-Ptakhine, Kahn A, Haase G. Adenoviral cardiotrophin-1 gene transfer protects pmn mice from progressive motor neuronopathy. J. Clin. Invest. 1999; 104: 1077-1085.

15.—Bustos M, Sangro B, Alzuguren P, Gil A, Ruiz J, Beraza N, Qian C, Garcia-Pardo A, Prieto J. Liver damage using suicide genes. A model for oval cell activation. Am. J. Pathol. 2000; 157(2): 549-559.

DETAILED DESCRIPTION OF THE INVENTION

For the purposes of the present invention:

i) active fraction of CT-1 means any partial polypeptide sequence of CT-1 that maintains the physiologic effects of the complete protein claimed in the present invention.

ii) polypeptide derivative with CT-1 activity means any polypeptide sequence that has a homology with native CT-1 greater than 80% and that maintains the physiologic effects of the complete protein claimed in the present invention.

iii) the polynucleotide sequences coding for the said active partial sequences of CT-1 or polypeptide derivatives of CT-1 described in i) and ii) are also to be understood as being covered by the present invention.

iv) cardiotrophin-1 or CT-1 means the native form of the protein, any form of recombinant protein (simple or in delayed-release formulations), any polynucleotide form that encodes or expresses the complete protein of CT-1, or by extension any of the forms described in i), ii) and iii).

The present invention is based on the discovery that the gene of CT-1 is overexpressed during the process of hepatic regeneration following surgical resection of a portion of the hepatic parenchyma, reaching maximum expression 48 hours after hepatectomy coinciding with the moment of maximum proliferation of hepatocytes. On the basis of this finding, the influence of CT-1 on the process of hepatic regeneration was investigated, and it was found that transduction of the hepatic parenchyma with gene sequences coding for CT-1 significantly stimulates hepatic regeneration after partial hepatectomy and prevents the death of the animal after subtotal hepatectomies. Similarly, it has been demonstrated that transduction of the liver with sequences coding for CT-1 provides highly efficient protection of the hepatocytes against a variety of hepatotoxic agents, markedly reducing the phenomena of hepatocellular apoptosis/necrosis. Finally, these findings demonstrate that CT-1 is a powerful protective agent of the hepatocytes against agents that cause cell death and in addition possesses the property of stimulating the processes of hepatic regeneration.

Accordingly, the present invention proposes and claims the use of CT-1, or of an active fraction of CT-1, or of a polypeptide derivative with CT-1 activity, or of a polynucleotide sequence that encodes and expresses CT-1, an active fraction of CT-1 or a polypeptide derivative with CT-1 activity, in the manufacture of compositions that can be used for stimulating hepatic regeneration after partial surgical resections of the liver or after hepatic lesions caused by chemical agents, biological agents, inflammatory or immunologic mediators and in addition as a hepatoprotective drug in the various forms of acute, subacute, fulminant or chronic hepatitis of toxic, viral, immunologic or metabolic etiology and for stimulating regeneration, protecting the hepatocytes and improving hepatic function in hepatic cirrhoses of alcoholic, viral, metabolic or immunologic etiology and in a transplanted liver.

EXAMPLES

1. Adenoviral Vector Containing the Gene Sequence Coding for CT-1 (AdCT-1)

A defective adenovirus (with deletion at E1 and E3) was constructed that contains the gene of cardiotrophin-1 (AdCT-1), which was carried out as described in detail below. The cDNA of murine CT-1 was obtained by selection from a library of mouse muscle cDNA with a PCR probe corresponding to nucleotides 20-639 of the mouse cDNA sequence (accession No. U18366 in GenBank). It was cloned in the pGEM-T/CT-1 vector and confirmed by sequencing. Next, the cDNA of CT-1 was cloned in the pKS vector to form pKS-CT-1 that contains an expression cassette made up of the Rous sarcoma virus promoter (RSV nucleotides 4526-5108 of M83237 GenBank), the peptide signal of nerve growth factor (NGF nucleotides 298-378 of V00836 GenBank), the cDNA of murine CT-1 (nucleotides 20-639 of U18366 GenBank) and the SV40 polyadenylation signal (nucleotides 2546-2775 of NC0016691 GenBank). This expression cassette was removed from the pKS-CT-1 plasmid by BamHI/SalI and was ligated to the pGY63 adenoviral shuttle plasmid at the HinfI site for forming the pGY63-CT-1 plasmid. This plasmid pGY63-CT-1 contains the left-hand adenoviral ITR (inverted terminal repeat), the packing signal (ps) and part of the pIX gene and between these last two there is the CT-1 expression cassette. This plasmid pGY63-CT-1 was cotransformed in electrocompetent *E. coli* SF800 cells together with pXL2689 containing the adenoviral genome for homologous recombination. The correct recombinants were digested with PacI and transfected in cells 293 (human embryonic renal cells transformed with DNA of adenovirus 5, ATCC reference number CRL-1573), for production of adenoviruses. The structure of AdCT-1 is presented in FIG. 1. The transformed strains of *E. coli* were deposited on 12th Sep. 2001 in the Spanish Type Culture Collection (CECT) (*E. Coli* PKSCT1, CECT No. 5980) in the University of Valencia (Burjasot, Valencia, Spain).

For production of a stock of adenovirus, cells 293 were employed, infected with the supernatant containing the recombinant adenovirus. The cells 293 were first sown in 6-well plates with an approximate confluence of 80% and using DMEM medium at 2%. After several hours, the culture medium was removed and the cells were infected with 0.5 µl of the supernatant that contains the recombinant adenovirus diluted in 3 ml of DEMEM. After incubation for 1 hour at 37° C., the inoculum was removed and 4 ml of agar was added. The cells were cultivated for a period of 5 to 7 days at 37° C. Using a Pasteur pipette, a sample of virus was collected from a viral plaque formed in the cell monolayer; the agar cylinder was resuspended in 500 µl of DMEM with 2% of fetal calf serum and was stored at −80° C. In order to identify the recombinant adenovirus, cells 293 were sown in 12-well plates and were then infected with 250 µl of the previously isolated virus. When cytopathic effects started to be observed, the cells were collected again from each well independently. Next, the cells were submitted to three processes of freezing and thawing for the purpose of disrupting them and releasing the maximum of viral particles. The cell lysate from each series was centrifuged for 10 min at 1500 rpm. The supernatant containing the virus was used for infecting once again cells 293 cultivated in 6-well plates. As soon as the cells began to show a rounded shape, the supernatant was collected and the presence of viruses was confirmed by detecting viral DNA and RNA in the said supernatant. The supernatant that displayed high levels of viral expression was selected for amplification with the aim of constructing the stock of the recombinant adenovirus.

The cells 293 were cultivated in 150-mm plates (between 50 and 100 plates) and were infected with adenovirus from the stock using a M.O.I. of 10 (10 plaque forming units -pfu-/cell). When the cells exhibited a cytopathic effect they were collected and centrifuged at 1500 rpm for 10 min, resuspended in Tris (pH 8) 0.1M and frozen at −80° C. until subsequent purification.

The recombinant adenovirus was purified using cesium chloride gradients. For this, the cells stored at −80° C. were resuspended in Tris 0.01M and were treated with 5% sodium deoxycholate at 1/10 ratio (v/v) for 30 min. Then, using a manual glass homogenizer, previously cooled, the cells were ruptured until a semi-liquid solution was obtained. Later on, the cellular extract was added to a saturated cesium chloride solution, maintaining a ratio of 5.8 ml of cesium chloride solution per 10 ml of cellular extract. This mixture was prepared in special heat-sealing polyhalomer tubes (Quick-seal, Beckman Instruments, CA, USA). Centrifugation was effected in a Beckman 50 Ti fixed-angle rotor at 35,000 rpm for 16-20 hours at 4° C. The band corresponding to the virus was collected using a sterile needle and syringe and was then submitted to a second centrifugation in the same conditions. Once extracted, the band was dialyzed against Tris 0.01M pH 8 at 4° C. during two independent processes each of 1.5 h. Aliquots of the virus preparation were placed in vials with sterile glycerol (ICN, USA) at 10% (v/v), frozen and kept in liquid nitrogen until they were used.

To determine the infective titer of the purified recombinant adenoviruses, the limiting dilution test was carried out in 96-well plates. This test is based on investigation of the cytopathic effect that the virus exerts on cells 293, determining the maximum decimal dilution of the suspension of virus capable of infecting and propagating in the cells 293. The cells 293 had previously been seeded in 96-well plates at $10^4$ cells per well. Next, the medium was removed from the wells and the cells were infected with adenovirus at a volume of 50 µl per well in progressive dilutions and in duplicate. Six hours later, 150 µl of fresh DMEM medium was added, and finally the cells were incubated at 37° C. for a maximum period of 7 days. After this period, the presence of cytopathic effects of the virus on the cells was evaluated. The titer was determined after multiplying the number of cells with cytopathic effect by the maximum dilution at which the effect was observed, and dividing the result by the total volume evaluated (0.05 ml), thus establishing the number of plaque-forming units (pfu) per ml. The determination was repeated at least three times for each sample.

2. CT-1, Recombinant Protein

The cDNA that codes for CT-1 was obtained from the pGEM-T/CT-1 plasmid by digestion with EcoR1 and was cloned in the pET28b vector (Novagen) (pET28b/CT-1). This vector supplies a sequence that codes for a series of histidine residues (1 kDa) and is translated in phase with the cloned cDNA to produce a fusion protein that contains, at its amino terminal end, a tail of histidines of 1 kDa and then the CT-1, with a thrombin cutting site between the two.

For production of the protein we used competent bacteria of the strain BL21 (DE3) (Novagen, Germany, Cat. No. 70235) as this strain contains a gene that is inducible by the RNA polymerase of T7, which is a necessary requirement for subsequent production of the protein. The competent bacteria were transformed with the vector obtained previously: pET14b (pET-14b vector from Novagen, Cat. No. 69660-3) with the cDNA of the cloned CT-1. The transformed bacteria were selected for growth in LB medium with ampicillin, as the vector contains a gene for resistance to this antibiotic.

For production of the recombinant CT-1, the transformed bacteria were grown on LB medium with ampicillin at 37° C. until the optical density was 0.4 at 600 nm. Then expression of the recombinant protein was induced with IPTG to a final concentration of 0.5 mM. In this way, the lac promoter is induced, and in consequence the promoter of the RNA polymerase of T7 that contains the vector and controls expression of the cloned cDNA. The culture was grown for a further 4 hours in the same conditions.

To obtain the extracts, once the bacteria had grown they were centrifuged at 4° C. The bacteria precipitated were resuspended in buffer of Tris/HCl 10 mM, sucrose 10%, 2-mercaptoethanol 2 mM and protease inhibitors. Homogenization was effected by sonication after incubation for 30 minutes with lysozyme at 4° C. This made it possible to disrupt the bacterial wall and improve the yield of the extraction process. The cytosolic extract was obtained by centrifuging the homogenate at 100,000 g for 90 minutes. Production of protein was verified by analyzing the cytosolic fraction by SDS-PAGE.

The His-CT-1 fusion protein was purified by chromatography of the cytosolic extract in a 2 ml Nickel column. After the column had been washed, the protein was eluted with 1 M imidazole. The pure protein was processed with thrombin and the CT-1 was recovered.

3. Northern Blot Assays for Measuring the Expression of CT-1 in vivo

The expression of genes of various cytokines (hepatocyte growth factor, HGF; LIF; Oncostatin; CNTF; CT-1) was analyzed during the process of hepatic regeneration using the Northern blot technique, after extracting mRNA from rat livers. Extraction of RNA was carried out by the guanidinium thiocyanate-phenol-chloroform method. Analysis by Northern blot was carried out as described by us previously (15), using the expression of 28S as load control and using probes that are specific for each of the genes analyzed.

4. Cellular Cultures of the Lines Derived from Hepatocytes

For the in vitro studies we used H35 cells, a hepatocellular line derived from rat hepatocarcinoma. The cells were cultivated in Dulbecco's modified Eagle medium (DMEM) supplemented with 10% of calf serum, glutamine 2 mM, streptomycin 100 U/ml, penicillin at 100 mg/ml. The cellular cultures were incubated at 37° C. in a 5% $CO_2$ atmosphere.

5. Techniques of Analysis of Apoptosis from the Cell Cycle and Expression of Annexin The cell cycle was analyzed using the method of DNA staining with propidium iodide. The cells ($0.5 \times 10^6$) were made permeable with 50 µl of a 0.1% solution of NP40 before staining with 0.5 µl of a 50 µg/ml solution of propidium iodide and 4 KU/ml RNAse (DNA-Prep Coulter reagents kit, Coulter). The cells were incubated at 37° C. for 20 min and then examined in the FACScalibur cytofluorometer. The cells that were positive for propidium iodide were analyzed in the "doublet discrimination module" DDM of the flow cytometer (FACScalibur, Becton-Dickinson, USA) excluding the doublets and using the FL3 parameter. The frequency of subdiploid cells defined the percentage of cells in apoptosis.

The presence of phosphatidyl serines oriented towards the cell exterior is one of the parameters that define a cell as apoptotic. Annexin V detects the apoptotic cells through its ability to bond to the phosphatidyl serine molecules presented towards the exterior of the cell membrane at the moment when the cell is determined as undergoing apoptosis. The cells ($0.5 \times 10^6$) were washed once in an incubation buffer containing: NaCl 140 mM, KCl 5 mM, $MgCl_2$ 1.2 mM, $CaCl_2$, and Hepes 10 mM. The cells were incubated in 100 µl of incubation buffer and 5 µl of fluorescein isothiocyanate conjugate coupled to the annexin V (Annexin-FITC), for 15 min at room temperature. Then the cells were examined with the FACScalibur, using the FL1 parameter. The apoptosis index was determined from the percentage of cells positive for Annexin-FITC.

6. Methods of Analysis of Proteins

Electrophoresis. For protein analysis, the cells were lysed in a lysis buffer (20 mM Tris pH 7.5; 150 mM NaCl, 1 mM EGTA, 1 mM EDTA, 1% Triton x-100, 2.5 mM sodium pyrophosphate, 1 mM, $Na_3VO_4$ 1 µg/ml of leupeptin, pepstatin, 10 µg/ml of trypsin inhibitor, 1 mM PMSF. The lysate of $0.5 \times 10^6$ cells was resuspended v/v in a migration buffer (125 mM Tris-HCl (pH 6.8), 10% sodium dodecylsulfate, 20%. glycerol, 100 mM dithiothreitol, 0.2% of bromophenol blue). The protein extract samples were heated at 100° C. for 5 min and were submitted to electrophoresis in a 10% polyacrylamide gel.

Immunodetection by Western blot. After electrophoresis, the proteins were transferred to nitrocellulose membranes in a transfer buffer (25 mM Tris, 0.2M glycine, 20% methanol, pH 8.5) at a current of 300 mA for 1 h. The transferred proteins were stained with a solution of ponceau red to verify successful transfer. Then the membranes were submitted to immunodetection of the specific proteins. For this, the membranes were blocked in a TBS-T incubation buffer (20 mM Tris, 137 mM NaCl, at pH 7.6 and 0.5% of Tween 20) with 2% of BSA (albumin fraction V) for 1 h. The membranes were incubated with specific antibodies directed against the protein under investigation for 2 h. Next, the membranes were washed with TBS-T buffer for 1 h and were then incubated again with protein G-HRPO (BIORAD) for 1 h. After washing several times in TBS-T buffer, the membranes were developed with chemoluminescence reagents (NEN Life Science Products) and were immediately submitted to exposure on hypersensitive films (Amersham) at predetermined times.

Immunoprecipitation. For the immunoprecipitation of specific proteins, the lysates of $10^6$ cells were incubated for 18 h in the presence of the specific antibody and 20 µl of protein G-Sepharose at 4° C. The immunocomplexes were isolated by centrifugation, washed twice in lysis buffer and dissolved in migration buffer. Next, the samples were heated to 100° C. and were submitted to migration by electrophoresis in 10% gels. Immunodetection of the specific proteins was carried out by Western blot.

7. Determination of DNA Synthesis, Assays of Proliferation

The H-35 cells were sown on 96-well plates. After 24 hours of serum deprivation they were stimulated with CT-1 (50 ng/ml) diluted in serum-free DMEN. After 24 hours of incubation with CT-1, marking was effected with 10-µCi/ml [methyl-$^3$H]-thymidine (ICN, Amersham) for 12 hours. The radioactive medium was removed and the cells were detached using 100 µl of trypsin at 37° C. collected in 25 µl of scintillation cocktail (Ecolite; ICN). Incorporation of [$^3$H]-thymidine was analyzed using a tri Carb 2900TR scintillation counter (Packard, Meriden, Conn.).

8. Tests in vivo of Hepatic Regeneration After Partial Hepatectomy (75% Surgical Resection)

The studies of hepatic regeneration were carried out in Fisher rats (males weighing 180 g). Surgical resection comprised 75% of the liver and the rats were sacrificed at different times (1 h, 3 h, 6 h, 10 h, 24 h, 48 h, 3 days, 6 days and 9 days). Liver samples were then taken and were divided into three parts for: histologic examination (fixed in Formol), immunohistochemical examination (fixed in OCT) and for RNA analysis (frozen in liquid nitrogen). A minimum of 4 rats were used for each time analyzed. The parameters of hepatic regeneration analyzed were the percentage of liver weight and expression of the nuclear antigen of cellular proliferation (PCNA) by immunohistochemistry.

8.1. Gene Expression of CT-1 During Hepatic Regeneration

The expression of genes of various cytokines (HGF, LIF, Oncostatin, CNTF, CT-1) was analyzed in the partial hepatectomy model for the purpose of studying its involvement in hepatic regeneration. In this study we analyzed samples from rat livers obtained at different times after partial hepatectomy (1 h, 3 h, 6 h, 10 h, 24 h, 48 h, 3 days, 6 days and 9 days). Each group comprised a minimum of 4 animals. In addition, livers from healthy rats without hepatectomy (controls) were analyzed. The corresponding mRNA levels of each cytokine were verified by Northern blotting. These experiments enabled us to make the entirely novel observation that the mRNA levels of CT-1 increase significantly at 24 and 48 hours post-hepatectomy (FIGS. 2 and 3) coinciding with maximum proliferation of hepatocytes, as demonstrated by the expression of PCNA and incorporation of bromodeoxyuridine (BrdU) by hepatocytes in immunohistochemical examination of the samples of liver tissue from the test animals. Furthermore, we were able to observe that the increase in transcriptional expression of CT-1 was preceded by a peak in the expression of HGF, which occurred at 10 hours after hepatectomy.

8.2. Effect of CT-1 on Hepatic Regeneration After Partial Hepatectomy

To study the role of CT-1 in hepatic regeneration, the adenovirus CT-1 (AdCT-1) was injected intravenously at a dose of $10^8$ pfU or the adenovirus with LacZ reporter gene (AdLac-Z) as control at the same dose. Surgical resection of 75% of the liver was carried out 48 h later. The rats were then sacrificed at the same times as stated previously. A minimum of 4 rats and a maximum of 8 rats were used for each time analyzed.

Administration of AdCT-1 induced an increase in the weight of the liver in the rats treated with AdCT-1 compared with those that received AdLac-Z with significant differences between the two groups at 48 hours, the time of maximum proliferation of hepatocytes (as demonstrated by immunostaining for PCNA in the liver samples obtained from these rats after hepatectomy). At 3 and 6 days after hepatectomy, the weight of the livers from the rats treated with AdCT-1 was greater than from the control rats, though at these times the differences between groups were not statistically significant (FIG. 4). These results show that the livers treated with CT-1 exhibit an acceleration of hepatic regeneration, with higher weights than the controls in the initial period after hepatectomy, but finally reaching values similar to the controls for the homeostatic mechanisms that control the final size of the hepatic viscus.

9. Assays in vivo of Hepatic Regeneration After Extended Hepatectomy (Surgical Resection >85%)

For the purpose of evaluating whether CT-1 could prevent the death of animals that had undergone subtotal hepatectomy, experiments were carried out in Fischer rats in which surgical resection of more than 85% of the liver was carried out. Two groups of 30 rats were used for this part of the experiments. One group was treated with AdLac-Z and the other group with AdCT-1 intravenously, at the doses mentioned previously. This type of surgical resection was performed 48 hours after administration of the adenovirus. The number of rats that survived the surgical resection fell to 14 rats for the AdLac-Z group and 13 rats for the group of those injected with AdCT-1. These rats were monitored for their long-term survival after the extensive surgical resection.

It was observed that in the first hour after hepatectomy, the mortality was 77% in the AdLac-Z group, whereas it did not reach 20% in the AdCT-1 group. Twenty-four hours after hepatectomy, only 7% of rats treated with AdLac-Z were alive, whereas the survival rate was 61% in the rats treated with AdCT-1; these differences are statistically significant. These percentages were maintained at the same values 4 days after surgery (FIG. 5). Our data indicate that CT-1 protects against mortality associated with extensive hepatic resections.

10. Protective Effect of CT-1 Against Apoptosis/Necrosis of Hepatocytes in vivo.

Tests of Fulminant Hepatic Damage

To evaluate the role of CT-1 in the modulation of hepatic damage caused by various harmful agents, Balb/c mice were used (males weighing 30 g), the hepatic damage being evaluated in three models of hepatocellular lesion: i) damage caused by intravenous administration of 100 mg/kg of concanavalin A, Con-A (Sigma, St. Louis, Mo., USA); ii) damage caused by the combination of intravenous administration of TNF$\alpha$ (Peprotech) (0.5 µg/mouse) and intraperitoneal administration of 25 mg of D-galactosamine, TNF$\alpha$/D-Gal (Sigma); iii) damage caused by intravenous administration of 1.5 µg/mouse anti-Fas (Jo2, Pharmingen). Six hours after administration of Con-A, or TNF$\alpha$/D-Gal or anti-Fas, blood was taken from the mice and they were sacrificed.

To determine the effect of CT-1 on the hepatic damage, a group "A" of mice was treated with saline solution, a group "B" with AdLac-Z ($10^7$ pfu) and a group "C" with AdCT-1 ($10^7$ pfu). After 48 hours, hepatic damage was induced in each group in the 3 models described in the preceding paragraph. A group of mice treated with saline serum, instead of the hepatitis inducer, was also included as a negative control (NC) of the experiment. Each group of animals comprised 5 mice. After 6 hours, the degree of hepatic damage was examined according to 2 parameters: measurement of transaminases (GPT) in serum by automated colorimetric assay (Technicon RA-1000, Bayer) and measurement of apoptosis by the TUNEL technique in liver samples fixed in OCT, using the "in situ death cell detection kit" (Roche Diagnostics GmbH, Indianapolis, Ind., USA).

Blood samples were taken from each mouse for the determination of transaminases, and immediately afterwards the animals were sacrificed and the livers were processed for histologic investigation (fixation in Formol) and investigation of apoptosis by the TUNEL technique (freezing in OCT).

In the first model of acute hepatic damage induced by the administration of Con-A, it was found that whereas the mice in the control groups (animals that had received saline or AdLac-Z) displayed some very high values of GPT, the levels of transaminases had barely changed in the animals treated with AdCT-1, and the differences between these and the mice in the control groups were highly significant (FIG. 6A). When the TUNEL technique was carried out on the hepatic tissue, we observed absence of apoptosis in the liver samples from mice treated with AdCT-1, compared with extensive regions of necrosis and apoptosis in the animals that had received saline serum or AdLac-Z prior to the administration of Con-A (FIG. 7).

In the second model of acute hepatic damage, induced by the administration of anti-Fas monoclonal antibody, we again observed that treatment with AdCT-1 prevented hepatocellular death (FIG. 6B). Six hours after administration of anti-Fas, the transaminase figure in the animals that had received AdCT-1 was observed to be considerably lower (with statistically significant differences) in those animals treated with AdCT-1 than in those that had received saline serum or AdLac-Z. Furthermore, in samples of liver tissue we observed, by the TUNEL technique and histologic examination, a large decrease in apoptotic bodies in the mice treated with AdCT-1 in comparison with the animals in the control groups.

The hepatoprotective role of CT-1 was also evaluated in a third model of hepatic lesion consisting of combined administration of TNFalpha and of D-galactosamine (TNF-$\alpha$/DGal). Six hours after the hepatic damage the transaminase levels, as well as the histological findings, showed a marked decrease in the figure for transaminases and in the number of apoptotic hepatocytes by the TUNEL technique in the mice treated with AdCT-1 compared with the mice in the control groups (FIG. 6C).

These data all show that CT-1 is able to protect liver cells against a variety of stimuli that cause hepatocellular apoptosis or necrosis.

11. Analysis of the Effect of CT-1 on the Cell Cycle and Survival in Hepatocytes Derived from Cell Lines Using the H35 rat liver cell line, we investigated the biological effects that recombinant CT-1 might exert as a cytokine regulator of apoptosis of hepatocytes. For the tests of stimulation with CT-1, the cells were previously depleted of serum for 18 h. The tests of stimulation with CT-1 were carried out in the absence of serum.

First we analyzed the effect of CT-1 on the cell cycle of this hepatocellular line. The cell cycle was determined by staining the DNA with propidium iodide followed by analysis by flow cytofluorometry. Apoptosis was induced by deprivation of serum in the culture medium of the cells for 4 days. The results showed that at 4 days of culture in these conditions, 86% of the H35 cells entered apoptosis. It could be seen that when CT-1 was present at a dose of 50 ng/ml and in the absence of any other costimulus, CT-1 was able to cause a marked delay in the start of apoptosis of H35 cells, which exhibited apoptosis in about 52% of the cells (FIG. 7).

Similar experiments were carried out by submitting H35 cell cultures to serum deprivation for 3 days and then measuring the cells' capacity for binding purified annexin coupled to FITC (fluorescein isothiocyanate) on their surface. Binding of annexin-FITC to the surface of the H35 cells was studied by means of analysis by flow cytofluorometry. This verified that whereas the cells cultivated in the absence of CT-1 exhibited about 21% positivity for annexin, those that had been treated with 50 ng/ml of CT-1 exhibited about 12% (FIG. 8). These experiments therefore confirmed that CT-1, at the dose used, is capable of exerting an antiapoptotic effect.

12. Analysis of the Effect of CT-1 on Cell Proliferation

Using the H-35 cell line, we investigated the capacity that CT-1 might have in DNA synthesis in hepatocytes. For this, 20,000 cells were sown per well in 96-well plates. To reveal possible stimulation, the cells had previously been depleted of serum for 24 hours. The tests of stimulation with CT-1 were effected in the absence of serum and at a dose of 50 ng/ml for 24 hours. The results showed that the cells cultivated in the presence of CT-1 exhibited a higher percentage of DNA synthesis than the control cells where CT-1 was not applied (FIG. 9). These experiments therefore confirmed that CT-1, at the dose used, is able to induce DNA synthesis.

13. Investigation and Analysis of the Signaling Pathways Induced by CT-1 in the Lines Derived from Hepatocytes The discovery that CT-1 exerts an antiapoptotic effect in hepatocytes both in vivo and in vitro led us to investigate the signaling pathways involved in stimulation of the CT-1 receptor in hepatocytes. Stimulation of receptors of the IL-6/LIF cytokine family leads to immediate phosphorylation of the signal transmitters belonging to the JAK-1 family. After stimulation of H35 with CT-1 at different times, we carried out immunoprecipitation of JAK-1 with a specific antibody (Cell Signaling Technology) from whole lysates of these cells. Using a specific antibody for phosphorylated tyrosines (4G10, Upstate Biotechnology) and Western blotting, it was verified that CT-1 induced tyrosine phosphorylation of the JAK-1 molecule at 5 minutes, the signal disappearing 60 min later (FIG. 10A).

Phosphorylation of STAT-3 is one of the activation pathways described that is involved in the signal of cytokines of the IL-6 family via JAK. Its activation by phosphorylation is associated with induction of cellular differentiation in some cases and hypertrophy in others (myocardiocytes). Using Western blotting, we analyzed lysates of H35 treated in vitro with 50 ng/ml of CT-1 at different times. Use of an antibody specific for phosphorylated STAT-3 (Santa Cruz Biotechnology) served to verify that CT-1 is capable of inducing phosphorylation of STAT-3 starting from 5 min post-stimulation, reaching a maximum at 30 min (FIG. 10B).

One of the pathways obviously involved in inhibition of the apoptotic signal is the PI-3/AKT pathway (phosphatidinositol-3 kinase/AKT kinase). Activation of PI-3K induces activation by phosphorylation of AKT in serine 475 and threonine 308. Activation of AKT causes, in its turn, phosphorylation of BAD in serines 112 and 136. BAD is a member of the Bcl-2 family and is an important regulator of the survival signal. Inactive BAD dimerizes with the Bcl-x or Bcl-2 proteins, neutralizing their antiapoptotic activity. Phosphorylation of BAD leads to release of Bcl-2 or Bcl-x which will suppress the apoptosis pathway. Therefore phosphorylation of BAD assumes there is suppression of the apoptosis pathway. In the present study we examined whether CT-1 could activate this survival pathway in H35's. After treatment of the cells with 50 ng/ml of CT-1 at different times, we then obtained the cytosolic fraction and, after that, immunoprecipitation of AKT with an anti-AKT polyclonal antibody (Cell Signaling Technology). Next, Western blotting was used for analyzing for presence of phosphorylated AKT by using a polyclonal antibody that is specific for the form of phosphorylated AKT in serine 475 (Cell Signaling Technology). It was confirmed that CT-1 induces phosphorylation of stable AKT in serine 475 at 15 and 30 min and then disappears at 60 min. Therefore CT-1 induces a survival signal in hepatocyte cell lines (FIG. 10C).

Summarizing, CT-1 is capable of inducing the JAK/STAT signaling pathway as well as the PI-3K/AKT survival pathway. Therefore the cascade of signals induced by CT-1 in hepatocytes explains how CT-1 acts as a cytokine with antiapoptotic effects via the PI-3k/AKT pathway and possibly as an inducer of proliferation and differentiation in hepatocytes via the JAK/STAT-3 pathway.

14. Investigation and Analysis of the Signaling Pathways Induced by AdCT-1 in in-vivo Models of Acute Liver Failure With the aim of analyzing the protective effect of AdCT-1 observed in the in-vivo models of acute hepatic damage in rat and mouse, the signaling pathways which, as had been observed in vitro, seem to be involved in stimulation of the CT-1 receptor in hepatocytes, were also studied in these in-vivo models.

As has previously been described in vitro, CT-1 is capable of inducing activation of the three principal pathways involved in survival or anti-apoptosis: STAT-3 (signal transducer and activator of transcription), PI-3K (phosphatidyl inositol 3-OH kinase)/AKT and Erk1/2 (extracellular regulated kinases).

a. Rat Model of Extensive Hepatectomy

As was confirmed in the experiments described in example 9 (hepatic resection >85%), the highest mortality was observed 1 hour after surgical resection (see FIG. 5). For this reason, said experiments were repeated with 3 treatment groups (AdCT-1, AdLac-Z and saline), but this time the rats were sacrificed 1 hour after surgical resection in order to take liver samples.

The liver samples collected were divided into three parts for histologic examination (fixed in Formol), immunohistochemical investigation (fixed in OCT) and for analysis of proteins (frozen in liquid nitrogen). From the samples frozen in liquid nitrogen, liver homogenates were obtained in lysis buffer (20 mM Tris pH 7.5; 150 mM NaCl; 1 mM EGTA; 1 mM EDTA; 1% Triton x-100; 2.5 mM sodium pyrophosphate; 1 mM $Na_3VO_4$ and a cocktail of antiproteases). By means of Western blots with specific antibodies obtained from Cell Signaling Technology (Beverly, Mass.), signaling was investigated in the three groups of rats: treated with AdCT-1, with AdLac-Z, and with saline (S). The antibodies used were anti-Stat-3, anti-phosphorylated-Stat-3 (Stat-3-Y-705), anti-AKT, anti-phosphorylated AKT (Akt-Ser-473), anti-Erk1/2, and anti-phosphorylated Erk1/2 which simultaneously detects the phosphorylated forms of Erk1 (Erk1-Thr-202) and Erk2 (Erk2-Y-204). In this way it was observed that the livers of rats treated with AdCT-1 exhibited phosphorylation of STAT-3, ERK1/2 and AKT in contrast to those of rats treated with AdLac-Z and saline, which did not exhibit this (FIG. 12A).

On the other hand, Caspasa-3 participates in the execution of apoptosis in response to many stimuli, including extensive hepatectomies (>85%). For this reason a test of caspasa-3 activity was carried out (CaspACE, Promega, Madison, Wis.), following the test protocol given by the company, on a proportion of the samples collected in liquid nitrogen. It was observed that the livers of rats previously treated with AdCT-1 displayed lower caspasa-3 activity compared with that observed in livers of rats treated with AdLac-Z and saline (FIG. 12B) thus indicating a lower apoptosis index in the former.

The foregoing suggests that the protective effect produced by AdCT-1 in hepatic damage in rats is provided by the initiation of cascades of antiapoptotic signals induced by CT-1 with consequent reduction of apoptosis, as is demonstrated by the low caspasa-3 activity encountered.

b. Mouse Model of Acute Hepatic Damage Induced by Concanavalin A

In order to study signaling in this model, the induction experiments were repeated with Con-A (see example 10) with 3 treatment groups (AdCT-1, AdLac-Z and saline), but this time the mice were sacrificed 1 hour after administration of Con-A. The liver samples obtained at the moment of sacrifice were processed in the manner described in example 14a above. Western blotting was carried out in the same way and using the same antibodies.

As can be seen in FIG. 13, treatment with AdCT-1 induced phosphorylation of AKT and ERK 1/2, the main antiapoptotic and survival pathways induced by CT-1. Therefore these results suggest that AdCT-1 protects mice against hepatic damage induced by Con-A by activating these main pathways of anti-apoptosis.

A.) Immunoprecipitation of cell lysates with antibodies specific to Jak-1. Then by Western blot with antibodies specific to phosphorylated tyrosines, phosphorylation of the Jak-1 molecule is observed at 5 minutes.

B.) Western blot with antibodies specific to phosphorylated Stat-3 (Stat-3-Y-705) where positivity is observed at 5 minutes of treatment.

C.) Immunoprecipitation of the cytosolic fraction with anti-AKT antibodies where subsequently, by Western blot with antibodies specific for the phosphorylated AKT form in serine 475 (AKT-Ser-475) induction is observed at 15 and 30 minutes.

Figure 1:
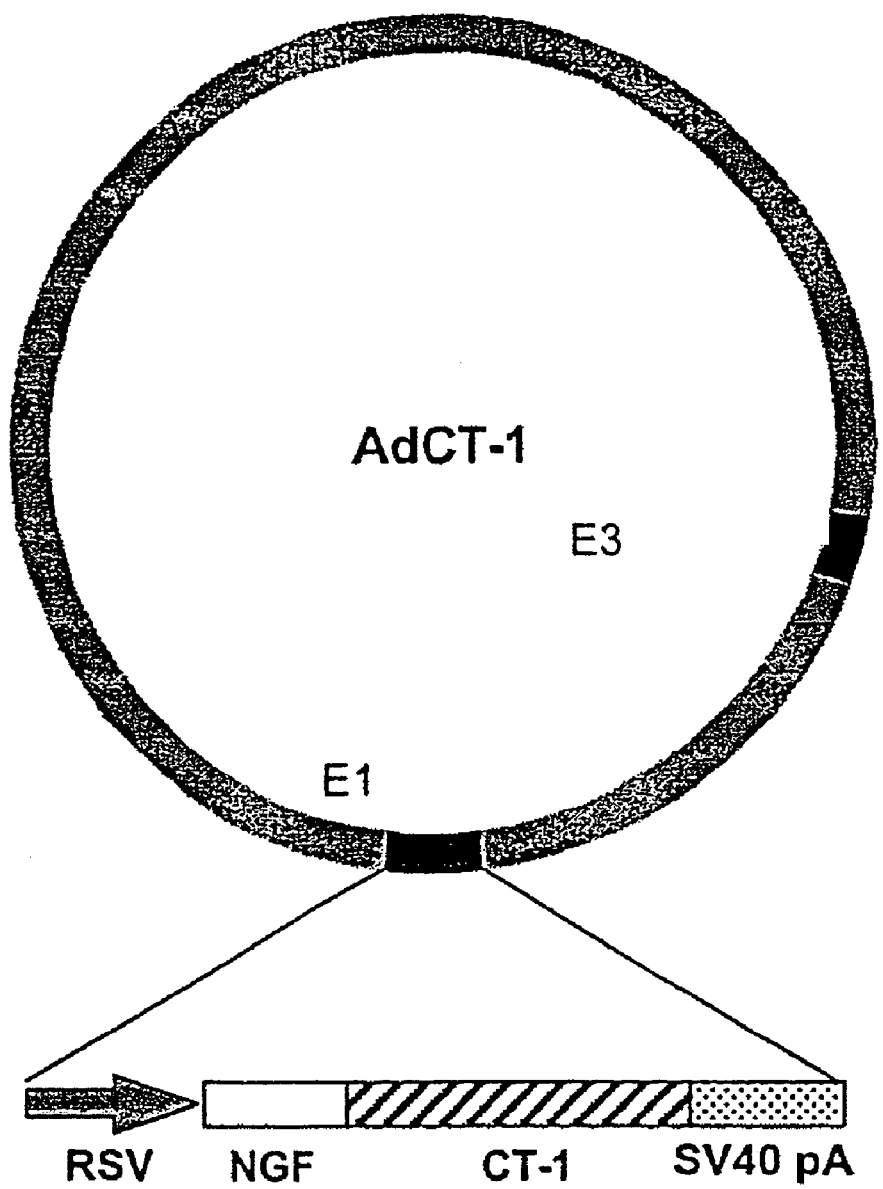
FIG. 1. Schematic of the structure of the AdCT-1 adenoviral vector containing the sequence coding for CT-1. RSV: promoter of the Rous sarcoma virus; NGF: peptide signal of nerve growth factor; CT-1: cDNA of murine CT-1; SV40: polyadenylation signal of the SV40 virus. The suppressed E1 and E3 regions are shown in black.
Figure 2:
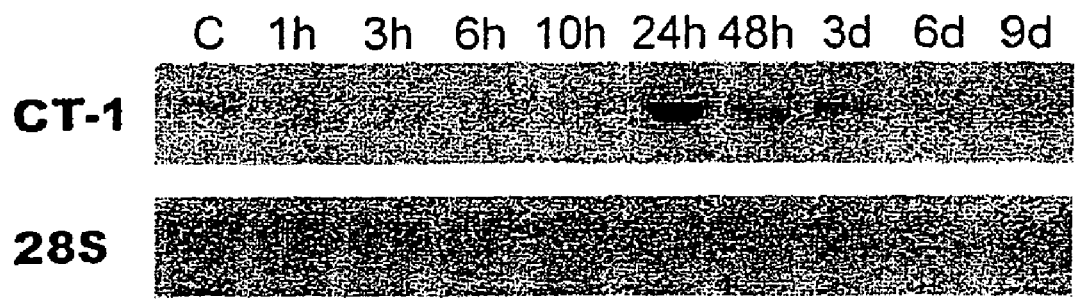
FIG. 2. Detection, by Northern blot, of the mRNA coding for CT-1 in rat liver samples obtained at different times (h=hours; d=days) after partial hepatectomy. 28S: rRNA as load control.
Figure 3:
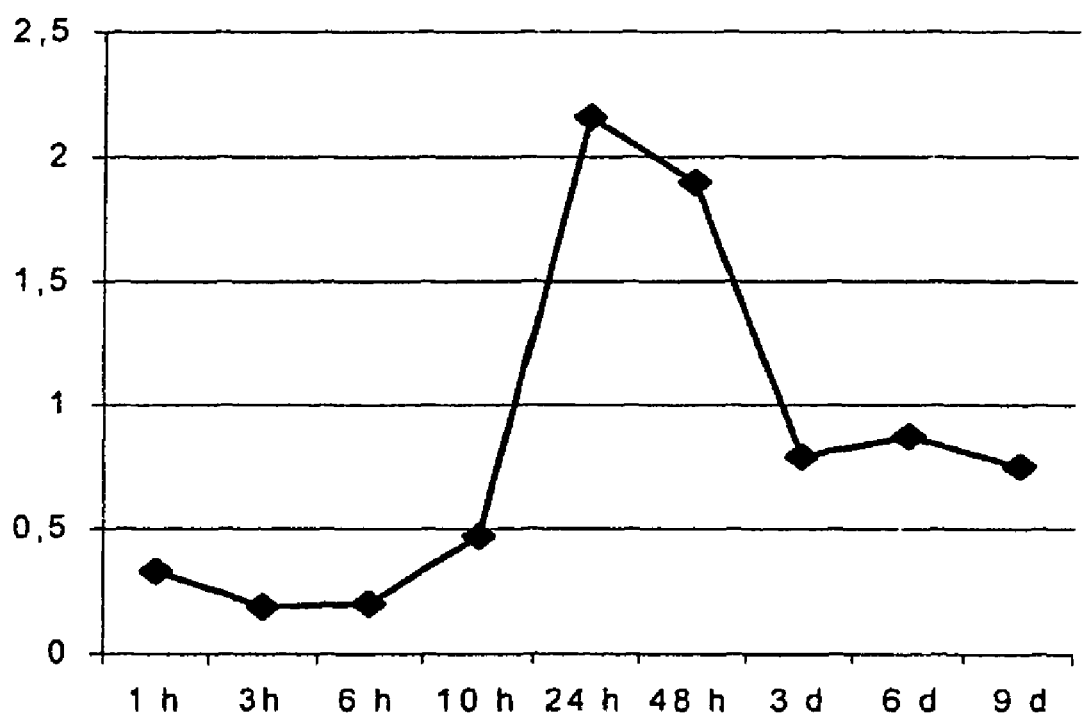
FIG. 3. Graphical representation of expression of CT-1 with passage of time (h=hours, d=days) in the Northern blot in FIG. 2. Ordinate: arbitrary units of optical density (CT-1/28S).
Figure 4:
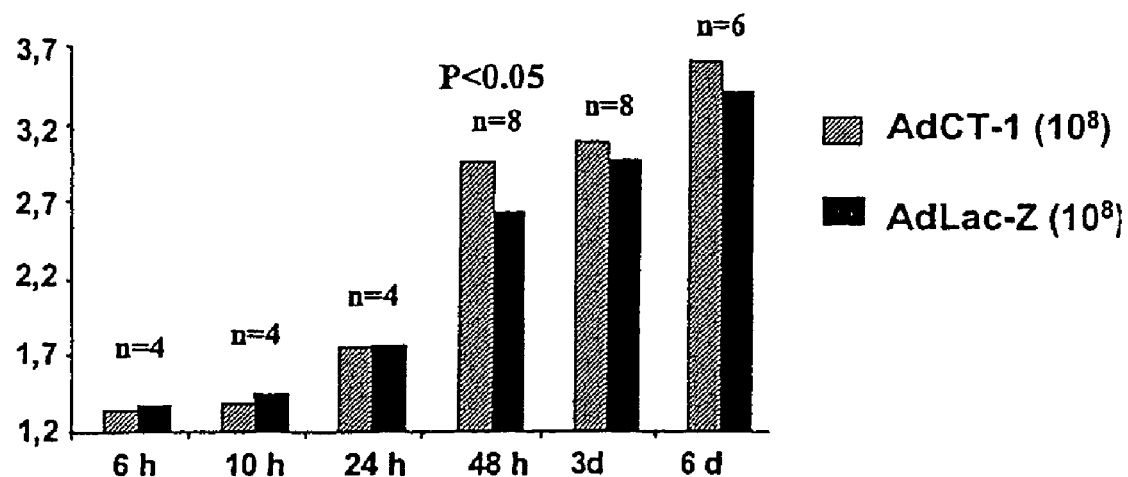
FIG. 4. Percentage of the weight of rat liver (on the ordinate) at different times (abscissa; h=hours, d=days) after partial hepatectomy before administration of AdCT-1 or AdLac-Z and after carrying out a partial hepatectomy.
Figure 5:
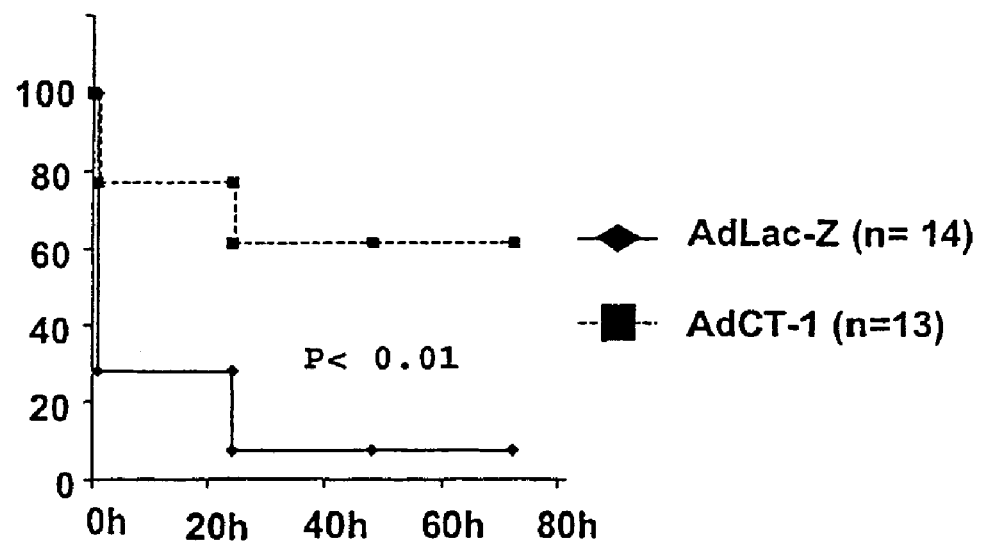
FIG. 5. Percentage survival (on the ordinate) for rats treated with AdCT-1 or AdLac-Z and hepatectomized (>85%) at 48 hours after the treatment. Abscissa: time (hours) after hepatectomy.
Figure 6A:
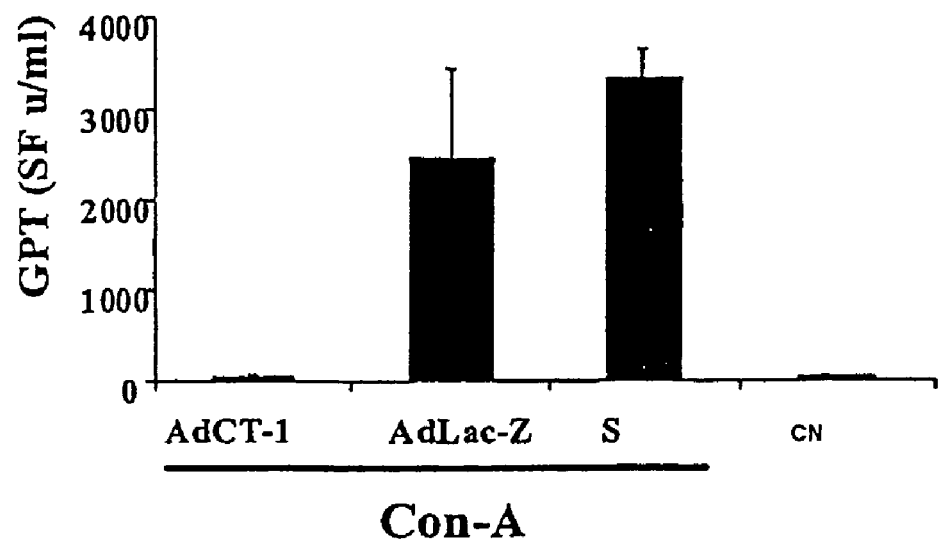
FIG. 6. Graphical representation of the serum levels of transaminases, GPT (on the ordinate, SF units/ml) and histologic images of hepatic tissue (TUNEL technique for visualization of apoptosis) from 3 models of induction of fulminant hepatitis in mice: by administration of concanavalin A, Con-A (FIG. 6A); by administration of the anti-Fas antibody (FIG. 6B); and by co-administration of TNFα and D-galactosamine, TNFα/D-Gal (FIG. 6C). 48 hours prior to induction of hepatitis, the animals were treated with an adenoviral vector (AdCT-1 or AdLac-Z), or with saline serum (S). Negative Control (NC) corresponds to a group of mice that were administered saline serum instead of the hepatitis inducing agent.
Figure 6A:
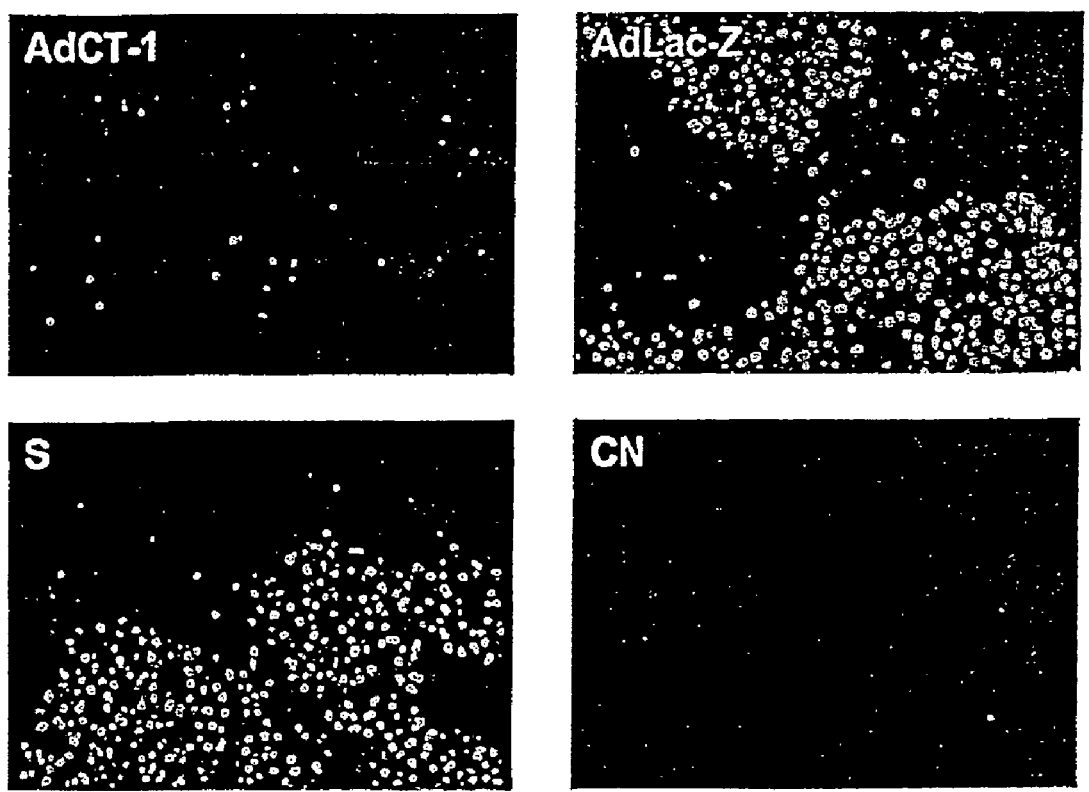
Figure 6B:
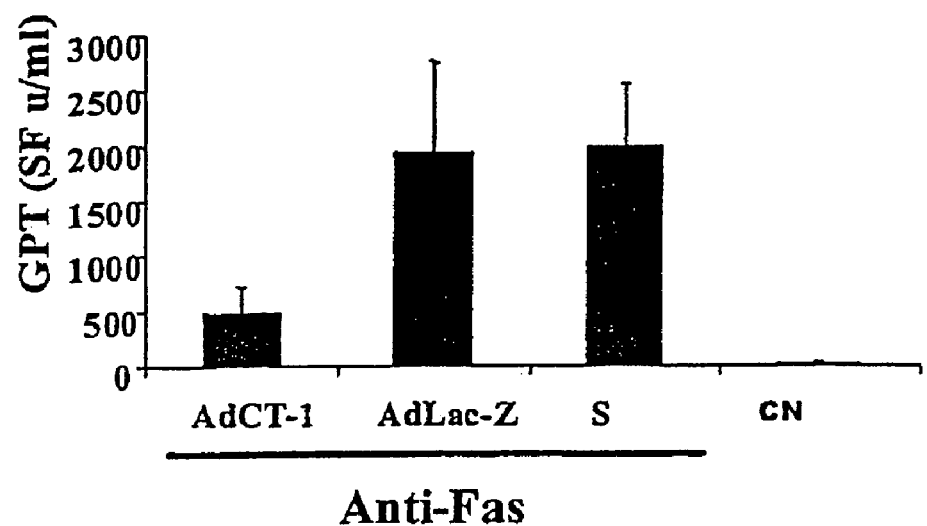
Figure 6B:
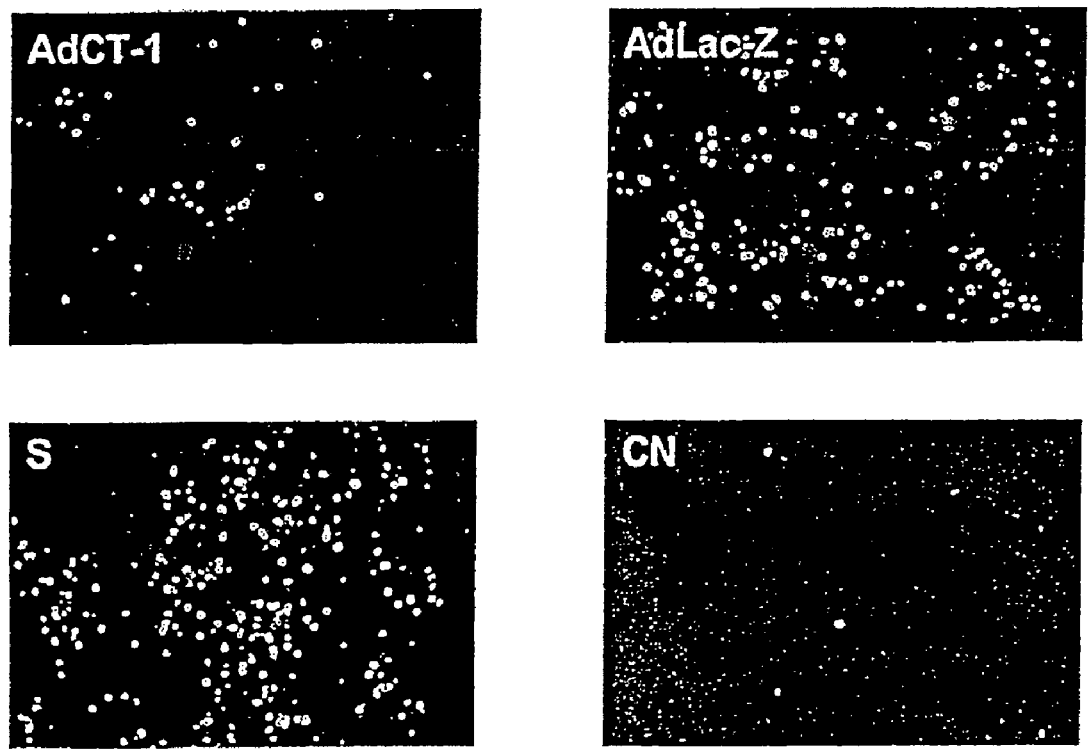
Figure 6C:
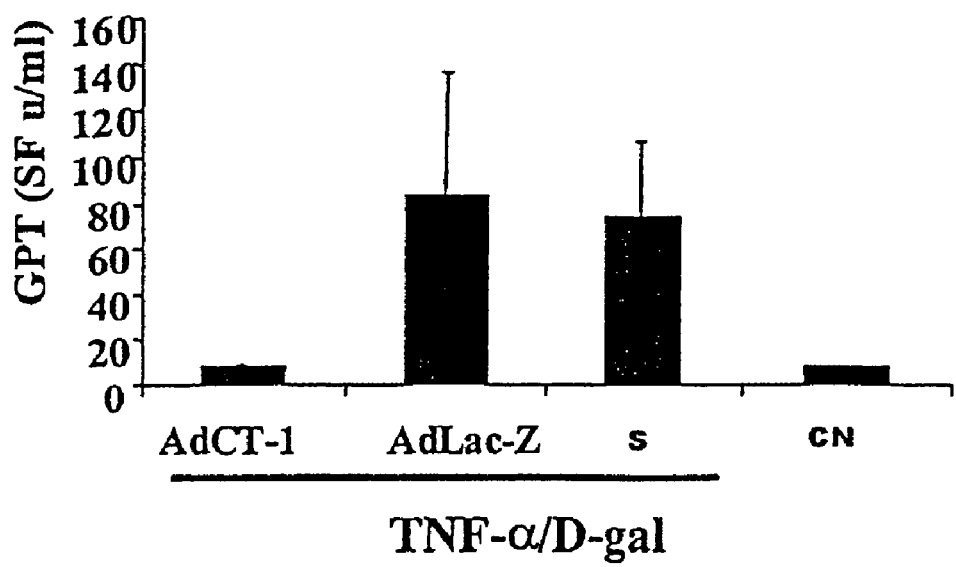
Figure 6C:
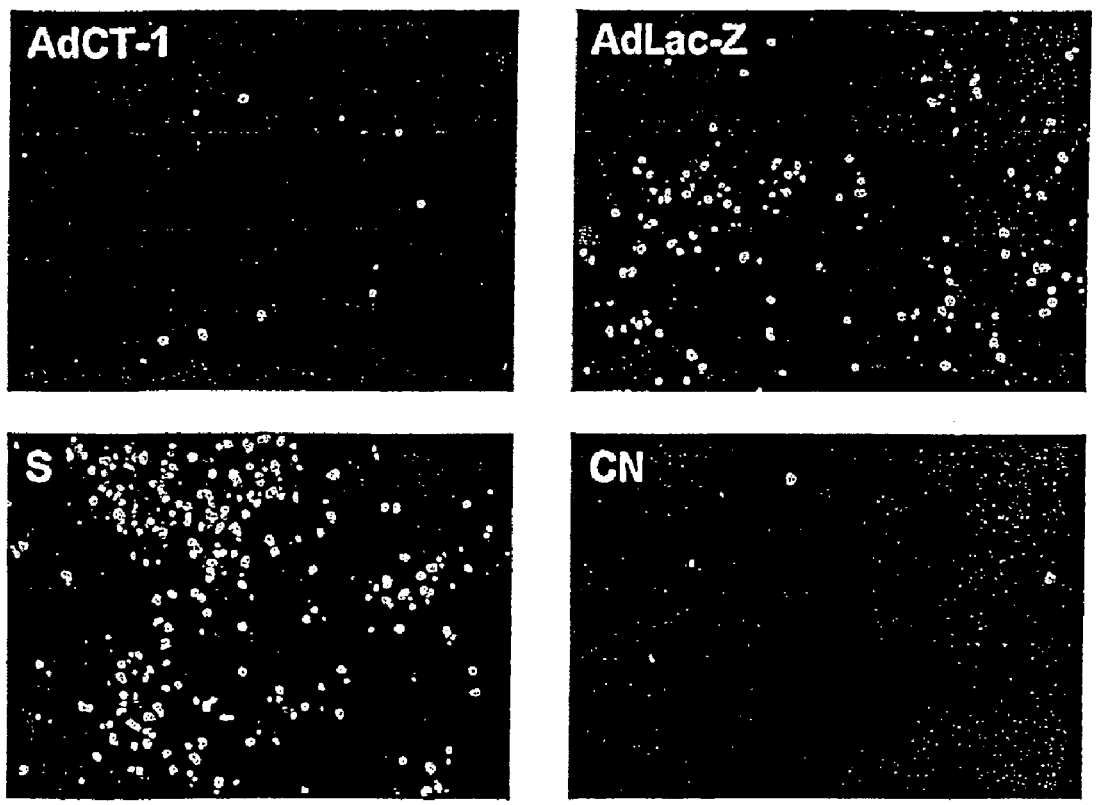
Figure 7:
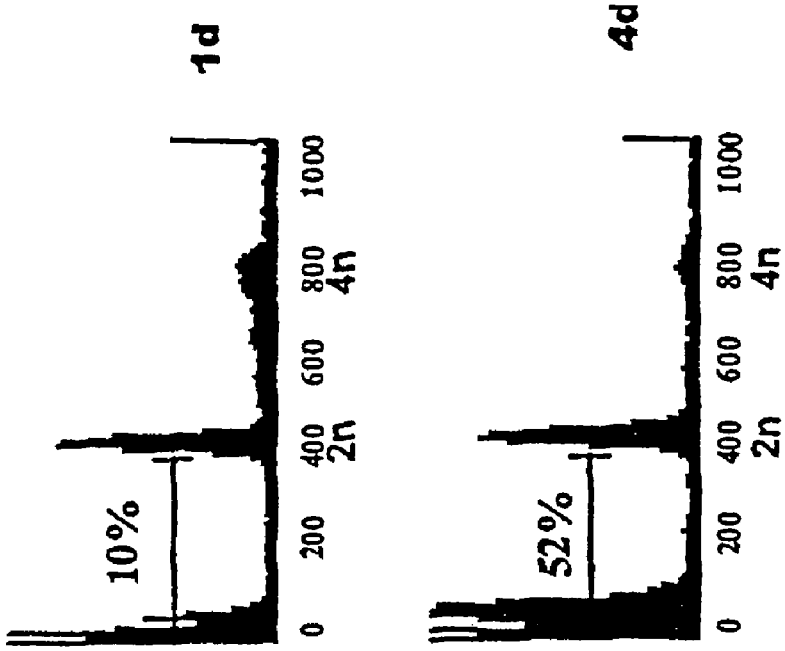
FIG. 7. Analysis of the cell cycle of H-35 cells after 1 day (top) and 4 days (bottom) after serum deprivation without presence of CT-1 (C=control) and in the presence of CT-1 (CT-1). Selected areas from left to right: Cells with DNA less than 2n (apoptotic cells, Apo); cells in G0-G1 (resting cells) and cells in S and M (proliferating cells). Ordinate: number of cells. Abscissa: DNA content.
Figure 7:
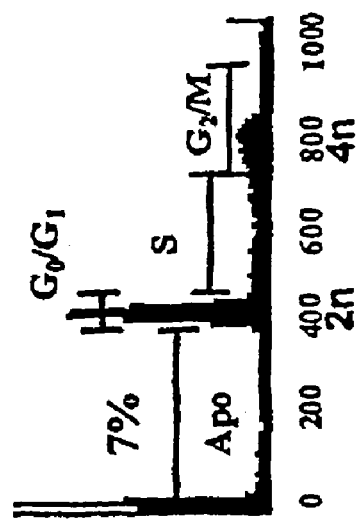
Figure 8:
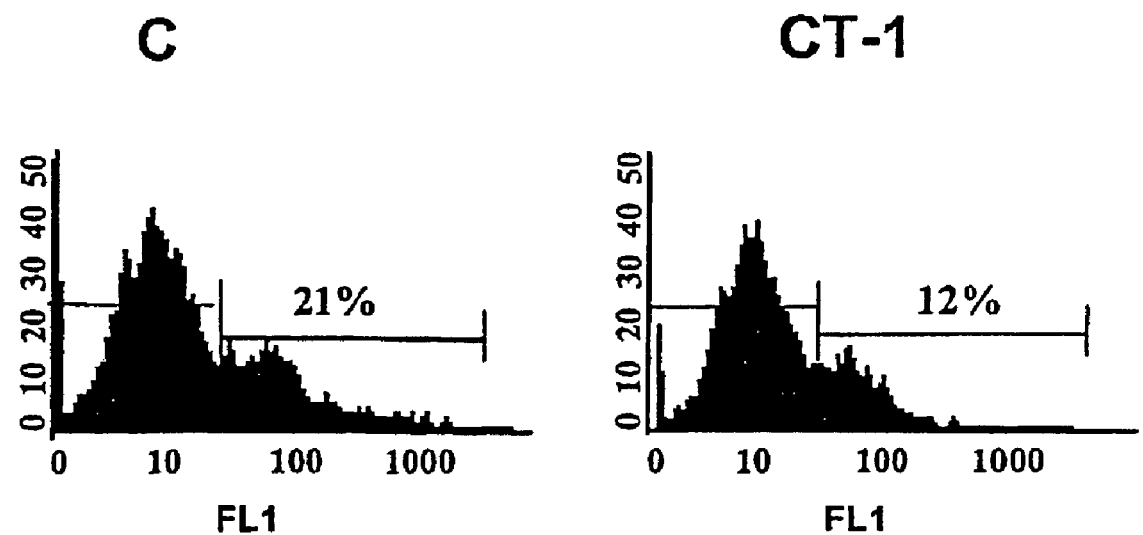
FIG. 8. Analysis of expression of annexin V in H-35 cells by flow cytometry after serum deprivation for 3 days without presence of CT-1 (C=control) and in the presence of CT-1 (CT-1). The cells cultivated with CT-1 exhibited about 12% of apoptotic cells, compared with the 21% of apoptotic cells observed in the absence of CT-1.
Figure 9:
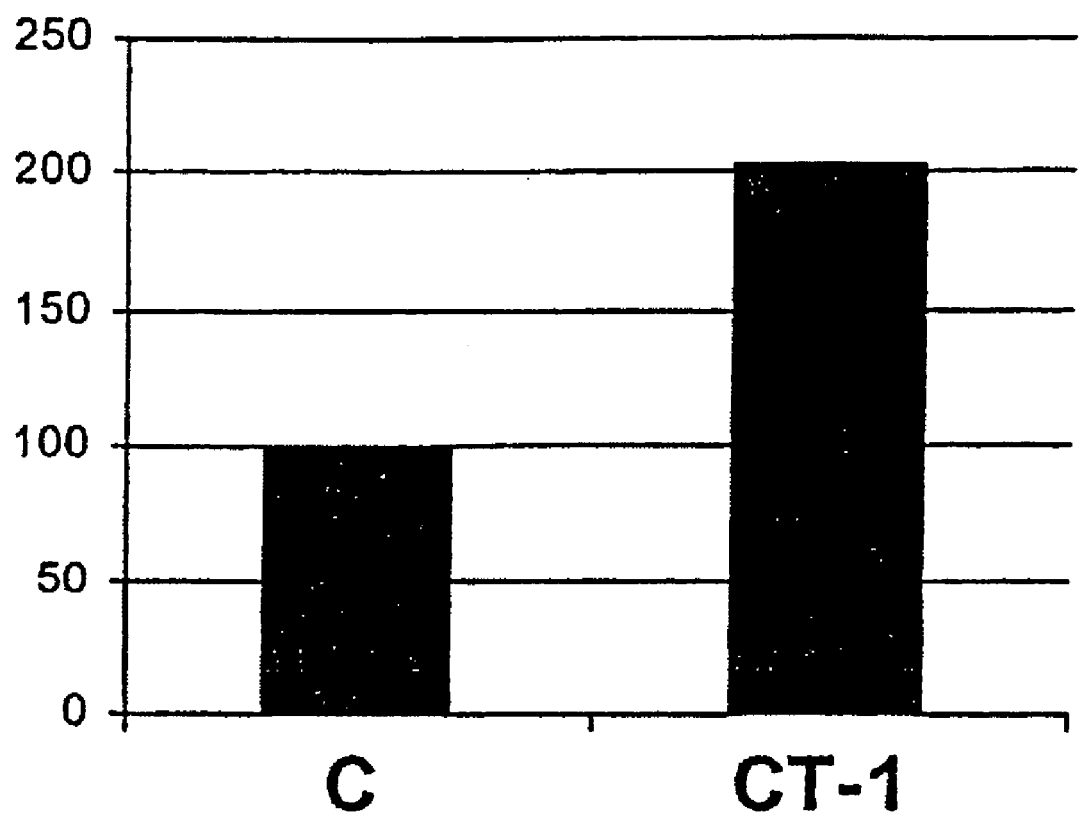
FIG. 9. Analysis of the effect of CT-1 on cell proliferation measured from incorporation of [$^3$H]thymidine. The results show the percentage increase (ordinate) in proliferation in the cells treated with CT-1 (CT-1) relative to the control cells without treatment (C=control).
Figure 10:
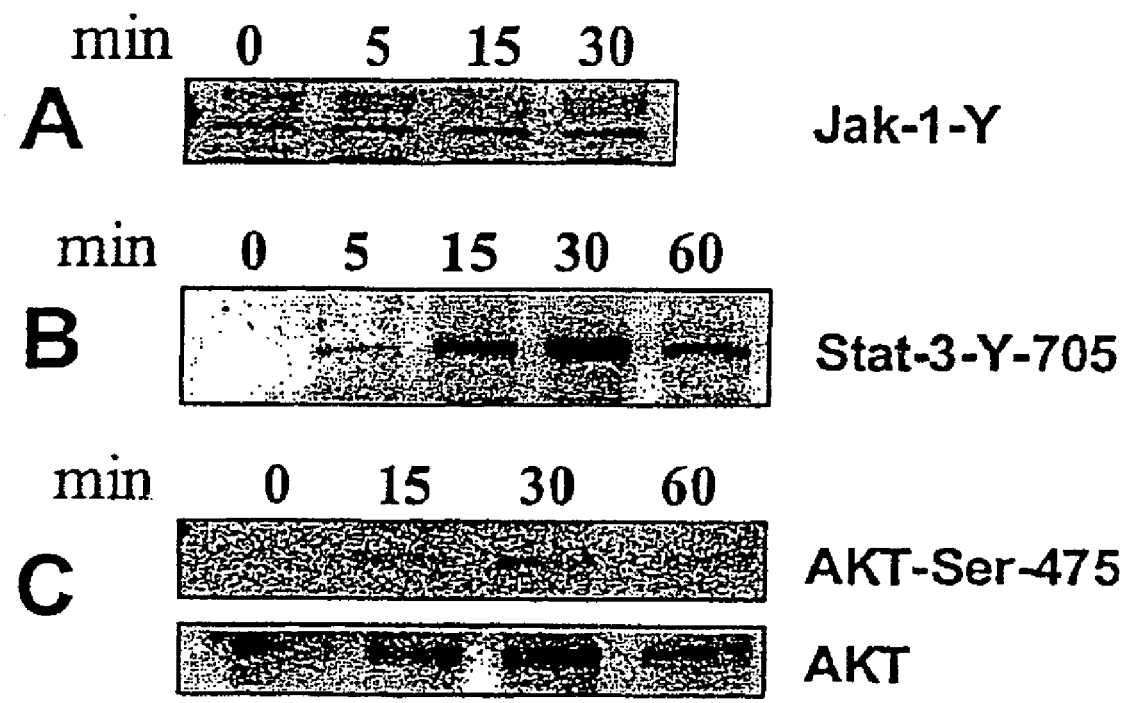
FIG. 10. Immunodetection of phosphorylated signaling proteins (Jak-1-Y, Stat-3-Y-705, and AKT-Ser-475) in H35 cell lysates taken at different times (minutes) after incubating the cells with CT-1.
Figure 11:
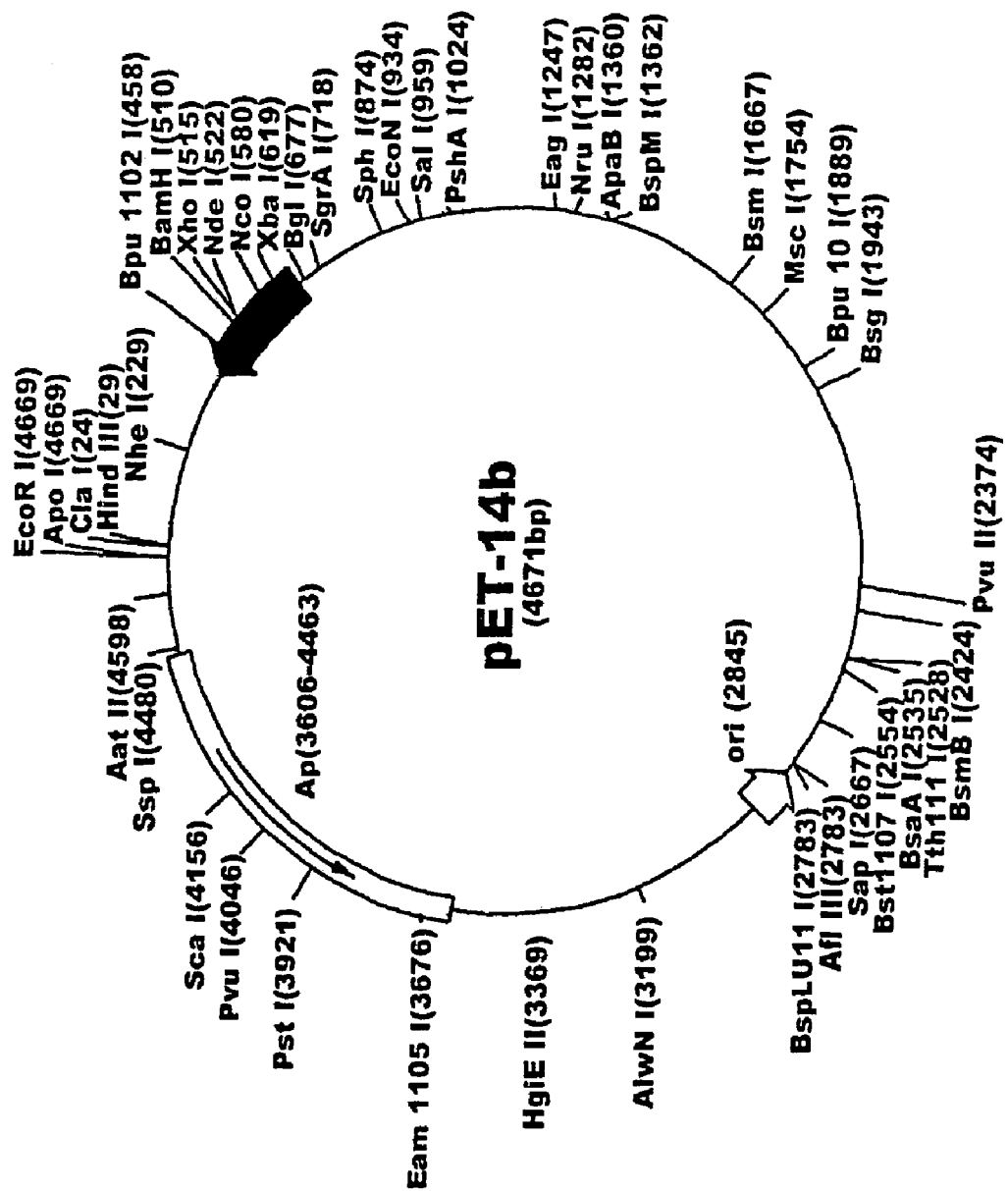

FIG. 11. Structure of the pET-14b vector.

Figure 12A:
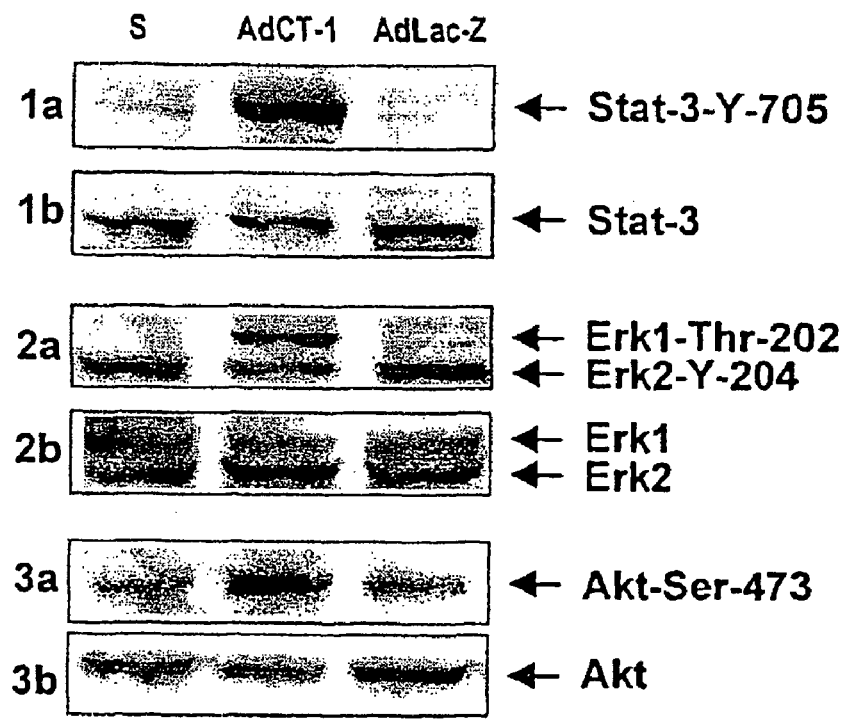

FIG. 12A. Western blot of signaling proteins in liver of rats treated with AdCT-1, AdLac-Z or saline (S), then submitted to hepatic resection greater than 85%, and sacrificed 1 hour after resection.

1a) Western blot with antibodies specific to phosphorylated Stat-3 (Stat-3-Y-705)

1b) Western blot with antibodies specific to Stat-3 for quantifying total Stat-3.

Phosphorylation of Stat-3 is observed in rats treated with AdCT-1.

2a) Western blot with antibodies specific to phosphorylated Erk1 and Erk2 (Erk1-Thr-202 and Erk2-Tyr-204)

2b) Western blot with antibodies specific to Erk1 and Erk2 for quantifying total Erk1 and Erk2.

Phosphorylation of ERK1/2 is observed in rats treated with AdCT-1.

5) Western blot with specific antibodies to phosphorylated Akt (Akt-Ser-473)

6) Western blot with antibodies specific to Akt for quantifying total Akt.

Phosphorylation of Akt is observed in rats treated with AdCT-1.

Figure 12B:
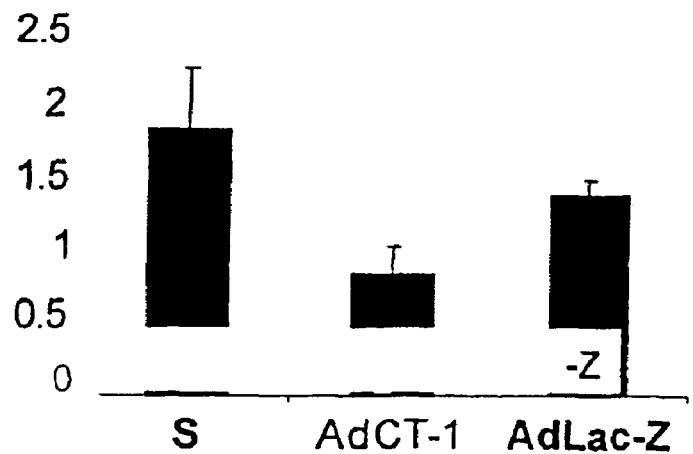

FIG. 12B. Caspasa-3 activity in the liver of rats that had undergone extensive hepatic resection (>85%). The samples are from the same groups of hepatectomized rats used in the experiments described in FIG. 12A. The chart shows the number of times the activity of caspasa-3 increases relative to healthy livers.

Figure 13:
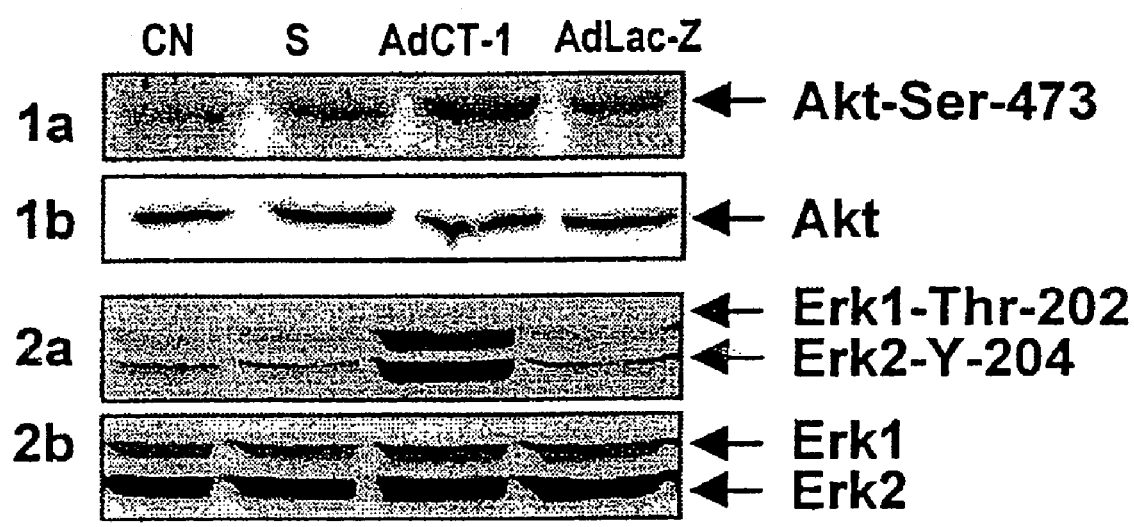

FIG. 13. Western blot of signaling proteins in the liver of mice treated with AdCT-1, AdLac-Z or saline (S) respectively, prior to administration of Con-A for inducing hepatic damage. The samples were taken at the moment of sacrifice, 1 hour after induction with Con-A.

1a) Western blot with antibodies specific to phosphorylated Akt (Akt-Ser-473)

1b) Western blot with antibodies specific to Akt for quantifying total Akt.

Phosphorylation of Akt is observed in rats treated with AdCT-1.

2a) Western blot with antibodies specific to phosphorylated Erk1 and Erk2 (Erk1-Thr-202 and Erk2-Tyr-204)

2b) Western blot with antibodies specific to Erk1 and Erk2 for quantifying total Erk1 and Erk2.

Phosphorylation of ERK 1/2 is observed in rats treated with AdCT-1.

The invention claimed is:

1. A method for treating a subject whose liver has experienced a loss of functional liver cells, the method comprising administering to the subject cardiotrophin-1 (CT-1) in an amount effective for exerting an antiapoptotic effect in hepatocytes of the subject and for stimulating DNA synthesis in hepatocytes of the subject or for proliferation or differentation of hepatocytes in the subject.

2. The method according to claim 1 wherein the subject has undergone surgical hepatectomy.

3. The method according to claim 1 wherein the subject suffers from a chronic liver disease.

4. The method according to claims 1 wherein the subject suffers from acute, subacute, fulminant or chronic hepatitis.

5. The method according to claim 1 wherein the subject suffers from hepatic cirrhosis.

6. The method according to claims 1, wherein the subject has undergone a liver transplant.

7. The method according to claim 1, wherein the loss of functional liver cells is induced by a stimulus selected from the group consisting of a toxic agent, a virus, an autoimmune disorder, ischemia, ischemia/reperfusion and an inflammatory process.

8. The method according to claim 7, wherein the loss of functional liver cells does not threaten the survival of the subject.

9. The method according to claim 8, wherein the stimulus is a toxic agent, ischemia, ischemia/reperfusion or an inflammatory process.

10. The method according to claim 8, wherein the stimulus comprises ischemia.

11. The method according to claim 1, wherein the subject suffers from a liver disease marked by an increased level of transaminases.

12. The method according to claim 11, wherein the liver disease is hepatitis.

13. A method for preventing damage to a liver in a subject in need of or subject to a hepatectomy or liver transplant comprising administration to the subject prior to the hepatectomy or transplant of an amount of cardiotrophin-1 (CT-1) effective to exert an antiapoptotic effect in hepatocytes of the subject.

14. The method according to claim 13, wherein the subject is in need of or subject to a hepatectomy.

15. The method according to claim 13, further comprising partially resecting the liver of the subject after the administration of the CT-1.

16. The method according to claim 13, wherein the subject is in need of or subject to a liver transplant.

* * * * *